United States Patent
Haraldsson et al.

(10) Patent No.: US 6,518,049 B1
(45) Date of Patent: Feb. 11, 2003

(54) LIPASE-CATALYSED ESTERIFICATION OF MARINE OIL

(75) Inventors: Gudmundur G. Haraldsson, Reykjavik (IS); Olav Thorstad, Heistad (NO); Bjørn Kristiansson, Reykjavik (IS)

(73) Assignee: Norsk Hydro ASA, Oslo (NO)

( * ) Notice: Subject to any disclaimer, the term of this patent is extended or adjusted under 35 U.S.C. 154(b) by 0 days.

(21) Appl. No.: 09/913,585

(22) PCT Filed: Feb. 16, 2000

(86) PCT No.: PCT/NO00/00056

§ 371 (c)(1),
(2), (4) Date: Nov. 2, 2001

(87) PCT Pub. No.: WO00/49117

PCT Pub. Date: Aug. 24, 2000

(30) Foreign Application Priority Data

Feb. 17, 1999 (NO) .................................................. 990739

(51) Int. Cl.[7] .............................. C12P 1/00; C12P 7/64
(52) U.S. Cl. .......................................... 435/134; 435/41
(58) Field of Search .................................... 435/134, 41

(56) References Cited

FOREIGN PATENT DOCUMENTS

| JP | 2303492 A | 12/1990 |
| JP | 07203979 A2 | 8/1995 |
| WO | WO 95/24459 | 9/1995 |
| WO | WO 98/18952 A1 | 5/1998 |

OTHER PUBLICATIONS

McNeill et al. (Lipase–Catalyzed Enrichment of Long–Chain Polyunstaturated Fatty Acids Jaocs, vol. 73, No. 11 (1996)).*
Moore, et al., "Production of Triglycerides Enriched in Long–Chain n–3 Polyunsaturated Fatty Acids from Fish Oil," JAOCS, 1996, vol. 73, No. 11, pp. 1409–1414.
McNeill, et al., "Lipase–Catalyzed Enrichment of Long–Chain Polyunsaturated Fatty Acids," JAOCS, 1996, vol. 73, No. 11, pp. 1439–1407.
Lie, et al., "Esterification of Polyunsaturated Fatty Acids with Lipases from Different Sources" Int'l J. of Food Science and Technology, 1992, vol. 27, pp. 73–76.
Shimada, et al., "Purification of Docosahexaenoic Acid by Selective Esterification of Fatty Acids from Tuna Oil with Rhizopus Delemar Lipase," JAOCS, 1997, vol. 74, No. 2, pp. 97–101.

* cited by examiner

Primary Examiner—Christopher R. Tate
Assistant Examiner—Randall Winston
(74) Attorney, Agent, or Firm—Fitzpatrick, Cella, Harper & Scinto

(57) ABSTRACT

Marine oil compositions which contain EPA and DHA as free acids are esterified with glycerol in the presence of a lipase catalyst under reduced pressure and essentially organic solvent-free conditions to form a free fatty acid fraction enriched in at least one of EPA and DHA.

27 Claims, No Drawings

LIPASE-CATALYSED ESTERIFICATION OF MARINE OIL

This invention relates to the lipase catalysed esterification of marine oils.

It is well known in the art to refine oil products of various kinds, including marine oils, with the aid of lipase catalysts whose specificity under the refining conditions employed enhances the recovery of a desired product.

For example, in PCT/WO95/00050 we disclosed a process for treating an oil composition containing saturated and unsaturated fatty acids in the form of triglycerides to transesterification reaction conditions with a $C_{1-6}$ alcohol such as ethanol under substantially anhydrous conditions in the presence of a lipase active to preferentially catalyse the transesterification of the saturated and monounsaturated fatty acids. With the preferred lipases, Pseudomonas sp. lipase (PSL) and *Pseudomonas fluorescens* lipase (PFL) it was possible to prepare from marine oil sources concentrates containing more than 70% by weight of the commercially and therapeutically important omega-3 polyunsaturated fatty acids EPA (eicosapentaenoic acid, C20:5) and DHA (docosahexaenoic acid, C22:6) in the form of glycerides.

A number of lipase-catalysed refining processes have utilised glycerol.

By way of example, JP 62-91188 (1987) teaches a process for preparing glycerides of polyunsaturated fatty acids (PUFA) in which the PUFA as free acid or ester is reacted with glycerol in the presence of a thermostable lipase. The fatty acid composition of the resulting glyceride product is substantially the same as in the starting PUFA.

WO91/16443 discloses a process for converting PUFA into triglycerides. The free fatty acids, for example mixtures of EPA and DHA, are reacted with about stoichiometric amounts of glycerol in the presence of a lipase, especially *Candida antarctica*, under essentially anhydrous, organic solvent-free, elevated temperature conditions with continuous removal of water and volatile alcohols. We are aware that there was little or no discrimination between EPA and DHA in this process.

In a paper in Int. J. Food Sci. Technol. (1992), 2, 73–76, Lie and Molin describe the esterification of a fish oil fatty acid concentrate with glycerol using three different lipases, including MML. Under the conditions used (5% water) they obtained a DHA-depleted free acid fraction (about 50% of the starting material) and a glyceride fraction with the same EPA content as the original fish oil concentrate. Thus, some selectivity was observed.

A paper by Myrnes et al in JAOCS, Vol. 72, No. 11 (1995), 1339–1344 discloses an organic solvent-free, lipase-catalysed glycerolysis of marine oils. A variety of different lipases are tested, and the reactions are run at low temperatures (12° C. or less) in the presence of relatively high (3.6%) amounts of water. Analysis of the resulting monoglyceride fraction showed, in some cases, good selectivity between unsaturated and saturated fatty acids, but no significant differences between individual PUFA.

Moore et al in JAOCS, Vol. 73, No. 11 (1996), 1409–1414 teach the hydrolysis of a fish oil in the presence of *Candida rugosa* lipase (CRL) to produce separate DHA-enriched and EPA-enriched fractions.

Subsequently, the EPA-enriched free fatty acid fraction is re-esterified with glycerol in the presence of *Rhizomucor miehei* lipase (MML).

A paper by McNeill et al in JAOCS, Vol. 73, No. 11 (1996), 1403–1407 discloses a MML-catalysed esterification of a n-3 PUFA concentrate with stoichiometric amounts of glycerol at 55° C. with continuous removal of water. The resulting triglyceride fraction contained the same level of DHA as the feed.

Finally, mention is made of WO96/37586 and WO96/37587. Example 3 of WO96/37586 discloses a process in which a free fatty acid concentrate originating in Chilean Fish Oil, comprising (after solvent fractionations of sodium salts) 25% EPA and 18% DHA, was directly esterified with glycerol using an immobilized *Candida rugosa* lipase (CRL) in the presence of 10% water at 35° C. After 120 hours, the extent of conversion had reached about 60%. In the glyceride mixture obtained, the triglycerides contained 28.2% EPA and 3.8% DHA and the monoglyceride fraction had 28.9% EPA and 4.5% DHA. The residual free fatty acids comprised 23.2% EPA and 31.5% DHA. This indicates good selectivity between EPA and DHA.

In contrast, in Examples 1 and 2, the MML catalysed re-esterification of a free fatty acid fraction with glycerol did not show significant selectivity between EPA and DHA.

The disclosure of WO96/37587 is similar to that of WO96/37586. Examples 1, 4, 6 and 8 show the glycerolysis of PUFA with MML without any discrimination between EPA and DHA.

It will be apparent from this, by no means exhaustive, discussion of the prior art that extensive research has been carried out in order to develop lipase-catalysed processes for isolating such commercially important PUFA as EPA and DHA from compositions such as fish oils containing them in relatively low concentrations.

We have now discovered a lipase-catalysed process for preparing concentrates of EPA and DHA by the direct esterification of free fatty acid from fish oil which, by selection of the lipase, permits the EPA/DHA contents of the resulting concentrate to be tailored to meet customers' different requirements.

More particularly, the present invention provides a process for esterifying a marine oil composition containing EPA and DHA as free fatty acids to form a free fatty acid fraction enriched in at least one of these fatty acids as compared to the starting composition, comprising the step of reacting said marine oil composition with glycerol in the presence of a lipase catalyst under reduced pressure and essentially organic solvent-free conditions, and recovering a free fatty acid fraction enriched in at least one of EPA and DHA.

The present invention is predicated on the discovery that glycerol can act as an excellent substrate for a lipase-catalysed direct esterification of marine oil free fatty acids, provided that certain critical reaction conditions are followed. This finding was not at all to be expected in view of the prior research using glycerol referred to above. The main esterification reaction can be schematically represented by the following equation in which the lipase catalyst is *Rhizomucor miehei* (MML):

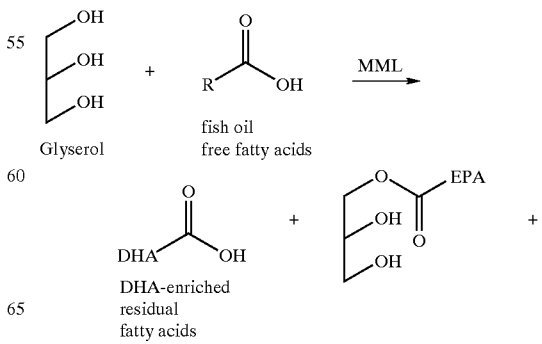

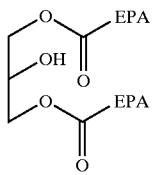

EPA-enriched 1(3)-
mono-and 1,3-mono
and 1,3-diglycerides
(and other EPA-enriched
glycerides not shown)

The product also contains other types of EPA-enriched glycerides, not shown in the schematic equation.

As will be discussed in more detail below, and illustrated in Example 8, the selection of the lipase catalyst can crucially affect the nature of the product. In the case of MML used in the illustrated reaction scheme, the product is a DHA-enriched free fatty acid fraction and an EPA-enriched glyceride fraction.

A significant feature of the present process is that it takes advantage of the fact that the selectivity of a lipase towards individual fatty acids is greater when they are in the form of free acids rather than as glycerides, since complications related to lipase regioselectivity or positioned selectivity are avoided. Surprisingly, the reaction with glycerol is far less successful when the EPA and DHA are present as esters, rather than as free acids, as is shown in Example 10 (Comparative) below.

The use in accordance with the present invention of glycerol as the substrate has the further advantage that it aids separation of the glyceride and free fatty acid product fractions by molecular distillation. The reason for this is considered to be that the esters of a trioic alcohol such as glycerol are less volatile than similar esters of short-chain alcohols such as methanol, ethanol and propanol.

It has been found that the relative amounts of glycerol are important to make the esterification reaction succeed. Preferably, a molar ratio of glycerol to free fatty acids in the starting composition of from 1:1.5 to 1:3 should be used, more preferably from 1:1.5 to 1:2.5. In our experimental work to date we have found that a molar ratio of about 1:2 of glycerol to fatty acids is optimal (corresponding to a ratio of available hydroxyl groups to free fatty acids of 1.5:1).

It is essential that the esterification reaction should be earned out under reduced pressure, in order to remove water from the reaction system as it is formed. This is necessary in order to make the reaction non-reversible, thereby making it possible to obtain high recoveries of the desired EPA/DHA products, Thus, the esterfication will generally be carried out at a pressure below 6665 Pa, and normally below 1.333 Pa e.g. from 133.3–1.333 Pa, although we have made the surprising observation that the reduced pressure conditions for optimum lipase activity is dependent to some extent on the particular lease used. Thus. in some cases it may be advantageous to use a pressure of front 1.333 to 133.3 Pa, and in the Examples which follow we report excellent results with pressures as low as 1.333–13.33 Pa. The optimum low pressure conditions for the particular lipase being used can, of course, be readily determined by routine experiments.

Organic solvents should be absent from the present process, unlike many prior art lipase-based systems, because organic solvents are volatile and will evaporate off under vacuum conditions.

The temperature at which the esterification reaction is conducted will depend on the marine oil composition being treated as well as on the lipase being used. It is desirable that the viscosity of the marine oil composition should be sufficiently low to enable the composition to be adequately agitated during the reaction, and for this reason it is often necessary to use temperatures of at least 20° C. On the other hand, too high temperatures are undesirable because high temperatures work against the kinetic resolution on which the fatty acid lipase discrimination is based, and also because the EPA and DHA can be destroyed by prolonged exposure to high temperatures, while lipases are also intolerant of high temperatures. Bearing factors such as these in mind, it is generally preferred to operate within the range of 20–40° C., often most preferably at 37–40° C., although temperatures of 0–20° C. may be used for fish oil compositions of high EPA and/or DHA contents where the composition remains sufficiently liquid at these low temperatures and conversely higher temperatures, in the range 40–70° C. may be possible for such stable immobilized lipases as MML and CAL.

The starting material for the present process can be any composition from a marine source containing EPA and DHA in free acid form. Such a composition may be obtained by saponification of crude fish oils, eg with sodium hydroxide, followed by acidification with eg sulphuric acid, according to standard procedures well known to those in the fish oil processing industries. Typically, the compositions will contain total contents of EPA and DHA in free acid form of 15–35% by weight, preferably 25–35%. Fish oils which are rich in DHA, such as tuna oil containing about 5% EPA and 25% DHA by weight are particularly suitable for preparing DHA concentrates by the process of the present invention, whilst fish oils rich in EPA (e.g. sardine oil with about 18% EPA and 12% DHA by weight) and Chile fish oil (20% EPA and 7% DHA by weight) are especially suitable raw materials for making EPA concentrates. However, it is an advantage of the present invention that cheaper fish oils with lower total EPA and DHA contents such as herring oil (about 6% EPA and about 8% DHA by weight) can be used as starting materials for the preparation of EPA and/or DHA-enriched fractions by the process of this invention, as shown in the Examples which follow later in this specification.

As mentioned earlier in this specification, it is a feature of the present process that it is possible to vary the nature of the enriched fractions by the choice of the lipase used. For example, the following effects are observed with the lipases noted:

i. a DHA-enriched free fatty acid fraction and an EPA-enriched glyceride fraction is obtained with with *Rhizomucor meihei* lipase (MML), *Mucor javanicus* lipase (MJL), and *Aspergillus niger* lipase (ANL); and ii. an EPA/DHA-endriched free fatty acid fraction and a glyceride fraction enriched in saturated fatty acids is obtained with Pseudomonas sp.—Amano AK (PSL), *Pseudomonas fluorescens*—Amano PS (PFL), *Rhizopus oryzae*—Amano F (ROL) and *Humicula Lanuginosa*—Amano CE (HLL), This ability to vary the nature of the product by appropriate selection of the lipase catalyst has the advantage that the operaton of the process can be tailored to suit customers' particular requirements. For example, one customer may require a DHA concentrate for supplementing infant feed, while another customer may require a mixed EPA/DHA concentrate for manufacturing a health product, but the requirements of both customers can be met simply by changing the lipase catalysts used.

Of course, yet more possibilities for tailoring the composition of the final product may be had by carrying out the process in two or more separate stages, with different lipase catalysts being used in the different stages.

The preferred lipases for the present process are *Rhizomucor miehei* (MML), which discriminates strongly between EPA and DHA; and Pseudomonas sp. (PSL), which discriminates between EPA and DHA, on the one hand, and the remaining fatty acids in fish oil on the other.

It is preferred, at least on the industrial scale, to use an immobilized form of the selected lipase, since it is found that not only does immobilization often increase the activity of the enzyme, especially at very low pressures, of the order of 1.333 to 133.3 Pa, but it also improves its stability and aids its recovery, which are all factors which affect the economics of the process.

Sufficient of the lipase should be used in order to effect the desired esterification reaction. In our work with immobilized MML we have used about 10% by weight of the immobilized product, based on the content of fatty acids in the marine composition being treated, which corresponds to a concentration of MML of about 1% by weight (the commercially available immobilized MML being about 10% lipase and 90% carrier).

In contrast, using non-immobilized lipases, we have utilized lipase concentrations of 10% by weight of the fatty acid content.

Following the completion of the esterification reaction, the product is separated in fractions containing mainly free fatty acids and glycerides respectively, by, molecular distillation.

The molecular distillation step to separate the free fatty acid fraction from the glyceride fraction can be performed at a temperature ranging from 100–200° C., but will normally lie in the range of 140–180° C. Its successfulness in terms of the achievable ratio residuum/distillate will depend on the vacuum. The vacuum may vary depending on factors such as the volatile components present in the mixture. It will generally be in the range of $1\times10^{-4}$–$1\times10^{-2}$ mbar, but a person skilled in the art can use the combination of the achievable vacuum, which in some instances may be outside the mentioned range, and a suitable temperature to achieve the desired end result.

Of course, the product from a first lipase-catalysed esterification may then be further concentrated in one or more subsequent lipase-catalysed esterifications, using the same or different lipase.

The free acid fraction which is obtained at the conclusion of the process may either be used as such, or if a product in free acid form is not acceptable for the intended use, then it can first be converted into ethyl ester, glyceride or other more acceptable form by any suitable method.

Likewise, in the case where the separated glyceride fraction contains EPA or DHA in economically worthwhile concentrations, this fraction may also be subjected to further treatment, for instance hydrolysis with aqueous alkali to form free acids, or esterification with ethanol to form ethyl esters of the fatty acids. The free fatty acid or ethyl ester fraction, thus formed may then, if desired, be further concentrated, e.g. by molecular distillation.

The esterification process of the present invention has a number of advantages which render it particularly suitable for industrialisation. The ability to tailor the composition of the products, especially by selection of the lipase catalyst, has already been mentioned, but further advantages which make the process attractive commercially include:

i. the high yields of highly concentrated EPA, DHA or EPA+DHA products which can be made, ii. the absence of any organic solvents, thus not only obviating the purification problems which the presence of such solvents can often cause, but also reducing the bulkiness of the process, which is important economically (less energy requirements, etc), iii. the ability to re-use immobilized lipase catalysts in several, perhaps up to 20 or more, successive runs, thus again contributing to keep costs down, iv. the ability to use any suitable marine oil composition which contains the polyunsaturated fatty acids of interest, and v. the overall simplicity of the esterification and subsequent separation processes.

The invention is illustrated by the Examples which follow, and in which area percentages are obtained by GLC analysis.

EXAMPLE 1

In this experiment a hydrolysis product of herring oil containing 5.6 area % of EPA and 8.0 area % DHA (in both cases as the free acid) was reacted with glycerol in the presence of *Rhizomucor miehei* lipase (MML; Novo's Lipozyme). The esterification conditions were:

MML: 10% dosage, by weight, based on the fatty acid substrate

Glycerol: 1 equivalent per two equivalents of free fatty acids (1.5 stoichiometric excess of hydroxyl groups)

Temperature: 40° C.

Pressure: 1.333 to 13.33 Pa

Organic solvent: None

The experimental procedure was as follows. To herring oil free fatty acids (10 g; M.wt. approx. 290 g/mol; approx. 34.5 mmol) and glycerol (1.56 g; M.wt. 92.1 g/mol; 17.3 mmol) was added immobilized *Mucor miehei* lipase (Novo's Upozyme, 1.0 g). The mixture was gently stirred at 40° C. on a magnetic stirrer hot-plate under a continuous vacuum of 1.333 to 13.33 Pa. The volatile water produced during the progress of the reaction was continuously condensed into a liquid nitrogen cooled trap. Titration was used to monitor the progress of the reaction. After the selected time the reaction was discontinued by separating off the enzyme by filtration. Fractionation was performed by preparative TLC on silica gel and each lipid fraction was subsequently fatty acid analysed by GLC after methylation by standard procedures.

The results are presented in Table 1 below:

TABLE 1

The progress of the direct esterification reaction of HO free fatty acids with glycerol by MML.

| | % Conv. (Titra- | Glycerides | | | | Residual Free fatty acids | | | |
| | | Area % | | Wt. % | | Area % | | Wt. % | |
| Time | tion) | EPA | DHA | EPA | DHA | EPA | DHA | EPA | DHA |
| 1 h | 30.4 | 3.4 | 0.5 | 14.5 | 1.4 | 8.1 | 15.7 | 84.5 | 98.6 |
| 2 h | 59.0 | 3.8 | 0.6 | 30.1 | 3.8 | 8.5 | 21.9 | 60.9 | 96.2 |
| 3 h | 60.2 | 4.7 | 1.0 | 45.3 | 5.5 | 8.6 | 26.2 | 54.7 | 94.5 |
| 7 h | 79.5 | 5.5 | 1.7 | 61.9 | 17.4 | 4.7 | 31.2 | 18.2 | 82.6 |
| 12 h | 87.4 | 6.0 | 2.3 | 92.2 | 25.5 | 3.5 | 46.7 | 7.8 | 74.5 |
| 24 h | 89.3 | 6.0 | 2.9 | 96.3 | 32.4 | 1.9 | 50.6 | 3.1 | 67.6 |
| 47 h | 89.9 | 6.5 | 3.1 | 95.7 | 32.9 | 2.6 | 56.2 | 4.3 | 67.1 |

After 7 h at 80% conversion the DHA to EPA ratio was 6.6:1 with DHA comprising 31% and EPA less than 5% of the residual free fatty acids. The DHA recovery was 83%. After 12 h that ratio had increased to 13:1 and after 24 h at 89% conversion to 27:1 with the recovery of DHA still nearly 70%. Beyond that level an equilibrium had clearly been obtained.

This experiment shows that, using MML as the lipase, the present invention enables a DHA concentrate to be prepared at a high conversion rate.

EXAMPLE 2
(Comparative)

Example 1 was repeated but with a reduced concentration of glycerol (3 equivalents of free fatty acids per equivalent of glycerol). The results are shown in Table 2 below:

TABLE 2

The progress of the direct esterification of HO free fatty acids with glycerol by MML at 40° C.

| Time | % Conv. (titration) | Glycerides Area % | | Glycerides Wt. % | | Residual Free fatty acids Area % | | Residual Free fatty acids Wt. % | |
|---|---|---|---|---|---|---|---|---|---|
| | | EPA | DHA | EPA | DHA | EPA | DHA | EPA | DHA |
| 0.5 h | 0.0 | 0.0 | 0.0 | 0.0 | 0.0 | 5.6 | 8.3 | 100 | 100 |
| 1 h | 8.5 | 0.0 | 0.0 | 0.0 | 0.0 | 6.9 | 10.3 | 100 | 100 |
| 2 h | 15.1 | 5.3 | 3.3 | 16.8 | 5.6 | 6.0 | 9.9 | 84.2 | 94.4 |
| 3 h | 21.5 | 5.7 | 3.5 | 27.0 | 7.2 | 7.7 | 12.4 | 73.0 | 92.8 |
| 6 h | 30.8 | 6.9 | 3.1 | 27.6 | 11.1 | 5.9 | 11.1 | 72.4 | 88.9 |
| 10 h | 34.7 | 6.6 | 3.0 | 33.7 | 11.8 | 6.3 | 11.9 | 66.3 | 88.2 |
| 24 h | 45.1 | 6.6 | 3.7 | 43.6 | 18.7 | 6.2 | 13.2 | 56.4 | 81.3 |
| 58 h | 72.1 | 6.1 | 5.5 | 72.7 | 45.1 | 6.3 | 17.3 | 27.3 | 54.9 |
| 80 h | 82.5 | 5.7 | 5.6 | 83.3 | 58.5 | 5.4 | 18.7 | 16.7 | 41.5 |

As will be noticed, the results in this experiment are far less satisfactory than those obtained for the 2:1 ratio used in Example 1. The reason for this change is not easy to explain. It may be related to insufficient availability of hydroxyl groups or an excessive amount of fatty acids, when it is taken into account that the mid-position of glycerol is far less available or at least far slower in its participation. The consequence is that equilibrium is reached far too early and there is no effective separation between EPA and DHA.

EXAMPLE 3

Example 1 was again repeated but the temperature at which the esterification reaction was conducted was varied between 30° and 60° C. The results are presented in Table 3 below:

TABLE 3

The progress of the direct esterification reaction of HO free fatty acids and glycerol by MML by varying the temperature

| Time (° C.) | % Conv. (titration) | Glycerides Area % | | Glycerides Wt. % | | Residual Free fatty acids Area % | | Residual Free fatty acids Wt. % | |
|---|---|---|---|---|---|---|---|---|---|
| | | EPA | DHA | EPA | DHA | EPA | DHA | EPA | DHA |
| 30 | 60.0 | 4.4 | 0.7 | 45.2 | 5.6 | 8.0 | 17.6 | 54.8 | 94.4 |
| 40 | 85.7 | 6.4 | 1.7 | 86.7 | 18.9 | 5.6 | 43.8 | 13.3 | 81.1 |
| 50 | 84.7 | 5.6 | 1.3 | 79.1 | 15.6 | 8.2 | 39.0 | 20.9 | 84.4 |
| 60 | 81.7 | 5.2 | 1.3 | 71.2 | 13.7 | 4.4 | 37.9 | 28.8 | 86.3 |

The results establish that 40° C. is the temperature of choice for these particular reaction conditions. At 30° C. agitation was difficult which explains the inferior results at that temperature. However, the favourable ratio between DHA and EPA, 8.6:1 at 60° C., compared to 8.0:1 at 40° C., is noticeable, since at that temperature a lower selectivity would be expected.

EXAMPLE 4

Example 1 was again repeated but varying the ratio between the glycerol and the free fatty acids at both 40° C. and 60° C. The results obtained are presented in Table 4 below:

TABLE 4

The progress of the direct esterification reaction of HO free fatty acids and glycerol by MML by varying the glycerol content.

| Gl/FFA ratio | % Conv. (titration) | Glycerides Area % | | Glycerides Wt. % | | Residual Free fatty acids Area % | | Residual Free fatty acids Wt. % | |
|---|---|---|---|---|---|---|---|---|---|
| | | EPA | DHA | EPA | DHA | EPA | DHA | EPA | DHA |
| 40° C. | | | | | | | | | |
| 1/1 | 84.4 | 5.7 | 2.0 | 63.7 | 22.5 | 11.2 | 37.2 | 32.3 | 77.5 |
| 1/2 | 84.3 | 6.2 | 2.0 | 71.4 | 21.1 | 9.3 | 40.2 | 28.6 | 78.9 |
| 1/3 | 67.8 | 6.3 | 2.5 | 77.9 | 19.7 | 7.3 | 21.4 | 22.1 | 80.3 |
| 60° C. | | | | | | | | | |
| 1/2 | 91.9 | 5.4 | 3.3 | 97.3 | 42.2 | 1.5 | 38.9 | 2.7 | 57.8 |
| 1/3 | 83.7 | 5.9 | 2.9 | 86.8 | 28.5 | 7.0 | 37.3 | 13.2 | 71.5 |
| 1/4 | 69.5 | 5.2 | 3.0 | 59.6 | 22.5 | 6.8 | 19.3 | 40.4 | 77.5 |

These results confirm the previous finding that a favourable DHA/EPA ratio, as well as a high recovery of DHA, can be obtained at 40° C. with 1:2 molar ratio between glycerol and free fatty acids.

EXAMPLE 5

This experiment shows the direct esterification of a free fatty acid composition obtained by hydrolysis from Chile fish oil using MML as the catalyst.

The Chile oil comprised 16.8 area % EPA and 12.3 area % DHA.

The esterification reaction conditions were the same as in Example 1. The results are shown in Table 5 below:

TABLE 5

The progress of the direct esterification reaction of Chile oil free fatty acids and glycerol with MML.

| Time | % Conv. | Glycerides Area % | | Glycerides Wt. % | | Residual Free fatty acids Area % | | Residual Free fatty acids Wt. % | |
|---|---|---|---|---|---|---|---|---|---|
| | | EPA | DHA | EPA | DHA | EPA | DHA | EPA | DHA |
| 1 h | 18.6 | 12.1 | 1.0 | 12.0 | 1.5 | 20.4 | 14.3 | 88.0 | 98.5 |
| 2 h | 39.4 | 14.3 | 1.2 | 31.4 | 4.0 | 20.4 | 18.7 | 68.7 | 96.0 |
| 3 h | 48.3 | 13.4 | 1.2 | 38.2 | 4.9 | 21.7 | 22.4 | 61.8 | 95.1 |
| 5 h | 53.6 | 16.3 | 1.4 | 45.4 | 5.5 | 22.1 | 28.1 | 54.6 | 94.4 |
| 7 h | 68.0 | 16.7 | 1.9 | 60.9 | 11.0 | 22.7 | 32.0 | 39.1 | 89.0 |
| 28 h | 80.0 | 20.1 | 3.5 | 85.9 | 21.6 | 13.2 | 50.0 | 14.1 | 78.4 |

The results in Table 5 show that the Chile oil is a suitable raw material for separating both EPA and DHA efficiently with MML. For instance, after 28 h reaction time 86% of the initial EPA had been separated into the glyceride fraction, whereas 78% of DHA remains in the residual fatty acid fraction comprising 50% DHA and 13% DHA.

EXAMPLE 6

Example 1 was again repeated using as the starting material crude tuna oil comprising 5.0% EPA and 18.2% DHA. The results are given in Table 6 below:

TABLE 6

The progress of the direct esterification reaction of tuna oil free fatty acids and glycerol with MML.

| | | Glycerides | | | | Residual Free fatty acids | | |
|---|---|---|---|---|---|---|---|---|
| | % | Area % | | Wt. % | | Area % | | Wt. % |
| Time | Conv. | EPA | DHA | EPA | DHA | EPA | DHA | EPA | DHA |
| 2 h | 55.2 | 4.8 | 2.0 | 42.3 | 5.6 | 8.1 | 42.2 | 57.7 | 94.4 |
| 4 h | 70.6 | 6.0 | 6.5 | 68.9 | 21.7 | 6.5 | 56.0 | 31.1 | 78.3 |
| 6 h | 77.1 | 5.3 | 3.6 | 73.2 | 14.0 | 5.6 | 64.3 | 26.8 | 86.0 |
| 8 h | 78.1 | 5.5 | 9.0 | 91.5 | 45.4 | 2.0 | 63.9 | 8.5 | 64.6 |
| 24 h | 89.0 | 4.6 | 16.4 | 91.1 | 76.9 | 3.7 | 39.7 | 8.9 | 23.1 |

Bearing in mind that the tuna oil used was crude and contained relatively low quantities of DHA, the results obtained were excellent.

EXAMPLE 7

Example 1 was repeated on a larger (100 g) scale. The same conditions were used as before with a 1:2 molar ratio between glycerol and free fatty acids under vacuum at 40° C. 10% dosage of MML was used and each reaction discontinued after 16 hours. After each run the lipase was filtered off on a sintered glass funnel under a stream of nitrogen atmosphere. When necessary the lipase was stored between runs under nitrogen at room temperature. The results of twenty consecutive runs are displayed in Table 7.

TABLE 7

Results of productivity studies of the direct esterification of free fatty acids from herring oil and glycerol with MML.

| | | Glycerides | | | | Residual Free fatty acids | | | |
|---|---|---|---|---|---|---|---|---|---|
| Run | % | Area % | | Wt. % | | Area % | | Wt. % | |
| No. | Conv. | EPA | DHA | EPA | DHA | EPA | DHA | EPA | DHA |
| 1 | 80.0 | 6.7 | 2.2 | 79.8 | 25.8 | 6.8 | 25.3 | 20.2 | 74.2 |
| 2 | 90.0 | 6.8 | 4.1 | 93.5 | 53.4 | 4.2 | 32.5 | 6.5 | 46.6 |

TABLE 7-continued

Results of productivity studies of the direct esterification of free fatty acids from herring oil and glycerol with MML.

| | | Glycerides | | | | Residual Free fatty acids | | | |
|---|---|---|---|---|---|---|---|---|---|
| Run | % | Area % | | Wt. % | | Area % | | Wt. % | |
| No. | Conv. | EPA | DHA | EPA | DHA | EPA | DHA | EPA | DHA |
| 3 | 92.3 | 7.3 | 5.1 | 96.0 | 62.4 | 3.6 | 36.6 | 4.0 | 37.6 |
| 4 | 92.5 | 6.9 | 3.2 | 93.4 | 53.2 | 6.0 | 34.4 | 6.6 | 46.8 |
| 5[a] | 89.9 | 6.0 | 4.4 | 92.6 | 67.1 | 4.3 | 19.3 | 7.4 | 32.9 |
| 6 | 91.1 | 6.7 | 5.5 | 91.4 | 60.8 | 6.5 | 36.1 | 8.6 | 39.2 |
| 7[a] | 83.0 | 6.8 | 6.2 | 82.3 | 58.3 | 7.1 | 21.7 | 17.7 | 41.7 |
| 8 | 89.3 | 5.6 | 3.5 | 86.2 | 50.1 | 7.4 | 28.9 | 13.8 | 49.9 |
| 9 | 88.1 | 5.5 | 3.3 | 89.4 | 42.9 | 4.8 | 32.6 | 10.6 | 57.1 |
| 10[b] | 55.0 | — | — | — | — | — | — | — | — |
| 11 | 90.1 | 9.6 | 3.2 | 92.6 | 38.6 | 7.0 | 46.4 | 7.4 | 61.4 |
| 12 | 93.2 | 7.3 | 5.4 | 95.1 | 64.0 | 5.2 | 41.3 | 4.9 | 36.0 |
| 13 | 93.7 | 6.0 | 4.8 | 93.9 | 57.8 | 3.8 | 34.3 | 6.1 | 42.2 |
| 14[a] | 86.4 | 5.3 | 4.6 | 85.3 | 56.1 | 5.8 | 22.7 | 14.7 | 43.9 |
| 15 | 93.0 | 6.2 | 5.7 | 95.0 | 68.5 | 4.4 | 34.6 | 5.0 | 31.5 |
| 16[a] | 87.9 | 7.5 | 5.0 | 91.9 | 59.0 | 4.9 | 25.3 | 8.1 | 41.0 |
| 17 | 91.1 | 5.6 | 4.5 | 92.3 | 55.0 | 4.7 | 37.6 | 7.7 | 45.0 |
| 18 | 93.5 | 6.4 | 4.0 | 95.4 | 93.5 | 4.4 | 33.4 | 4.6 | 36.5 |
| 19 | 91.2 | 6.1 | 4.2 | 91.9 | 54.4 | 5.6 | 36.5 | 8.1 | 45.6 |
| 20 | 90.0 | 7.2 | 3.5 | 91.5 | 47.4 | 6.1 | 35.4 | 8.5 | 52.6 |

[a]) This sample was not collected for the molecular distillation separation
[b]) This sample was neither analysed nor collected for the molecular distillation As will be noticed from Table 7 the lipase retained its activity during the twenty successive runs without any significant deterioration.

EXAMPLE 8

The purpose of this experiment was to demonstrate that lipases other than MML can be used in the process according to the present invention.

Seventeen (17) different lipase or lipase preparations were tested under similar reaction conditions to those used in Example 1 but at higher pressures, in the range from 133.3 to 2666 Pa, using the same herring oil as in Example 7 and with a fixed reaction time of 16 hours. Titration was used to monitor the extent of conversion. The glyceride mixture was separated from the residual free fatty acids by aid of preparative TLC in cases which displayed some activity and the fatty acid composition of the two resulting fractions determined by GLC. The results are given in Table 8 below.

TABLE 8

Results of the using of various lipases in the direct esterification reaction of free fatty acids from herring oil and glycerol.

| | | Glycerides | | | | Residual Free fatty acids | | | |
|---|---|---|---|---|---|---|---|---|---|
| | | Area % | | Wt. % | | Area % | | Wt. % | |
| Lipase | % Conv. | EPA | DHA | EPA | DHA | EPA | DHA | EPA | DHA |
| PSL | 17.4 | 0 | 0 | 0 | 0 | 4.4 | 5.6 | 100 | 100 |
| PFL | 23.5 | 0 | 0 | 0 | 0 | 6.1 | 7.9 | 100 | 100 |
| CAL[a] | 75.9 | 6.5 | 7.7 | 75.3 | 72.1 | 6.7 | 9.3 | 24.7 | 27.9 |
| CAL[a] | 69.2 | 5.8 | 8.5 | 66.1 | 70.9 | 6.7 | 7.8 | 33.9 | 29.1 |
| MJL | 71.8 | 4.0 | 0 | 62.2 | 0 | 6.2 | 10.3 | 37.8 | 100 |
| LNL[c] | 40.2 | 0 | 0 | 0 | 0 | 6.4 | 9.2 | 100 | 100 |
| PRL | 17.9 | 4.8 | 8.2 | 15.1 | 17.1 | 5.8 | 8.6 | 84.9 | 82.9 |
| ANL | 20.4 | 4.7 | 0 | 20.1 | 0 | 4.8 | 6.1 | 79.9 | 100 |
| ROL | 31.6 | 0 | 0 | 0 | 0 | 5.7 | 7.0 | 100 | 100 |

TABLE 8-continued

Results of the using of various lipases in the direct esterification reaction of free fatty acids from herring oil and glycerol.

| | | Glycerides | | | | Residual Free fatty acids | | | |
| | | Area % | | Wt. % | | Area % | | Wt. % | |
| Lipase | % Conv. | EPA | DHA | EPA | DHA | EPA | DHA | EPA | DHA |
| --- | --- | --- | --- | --- | --- | --- | --- | --- | --- |
| PCL | 0 | — | — | — | — | — | — | — | — |
| HLL | 32.4 | 0 | 0 | 0 | 0 | 1.1 | 1.5 | 100 | 100 |
| RDL | 0 | — | — | — | — | — | — | — | — |
| CLL | 0 | — | — | — | — | — | — | — | — |
| MML[d] | 76.0 | — | — | — | — | — | — | — | — |
| PPL | 24.4 | 4.3 | 6.3 | 19.3 | 22.0 | 5.7 | 7.2 | 80.7 | 78.0 |
| RNL | 11.9 | 3.9 | 1.6 | 18.2 | 3.6 | 2.4 | 5.6 | 81.8 | 96.4 |

[a] Lipase SP 382 from Novo Nordisk.
[b] Lipase SP 435 from Novo Nordisk.
[c] Lipase N con. 05501.
[d] MML was included for a comparison of the extent of conversion. Not analysed further.

It is interesting to notice from the table that the *Mucor javanicus* lipase (MJL) from Amano appears to discriminate strongly between EPA and DHA under these conditions and displayed a high activity. A similar behaviour of discriminating between EPA and DHA in favour of EPA was also displayed by the *Aspergillus niger* lipase (ANL), and also the *Rhizopus niveus* lipase (RNL), but the activity was much lower. PSL and PFL displayed activity under these conditions without discriminating significantly between EPA and DHA. These lipases are therefore suitable for concentrating both EPA and DHA together from fish oil under these conditions. The LNL, ROL and HLL are also shown to be useful in concentrating both EPA and DHA in fish oil, since they display a high activity.

In contrast, the *Candida antarctica* lipase, although displaying high activity, comparable to that of MML, did not discriminate between EPA and DHA in their action, nor did they display a strong discrimination between them and other fatty acids present in the fish oil. CAL is therefore not suitable for use under these conditions.

EXAMPLE 9

(Comparative)

Example 8 was repeated for several of the lipases but using a considerably higher vacuum of 1.333–13.33 Pa. The results are presented in Table 9 below:

TABLE 9

The progress of the direct esterification reaction under high vacuum of sardine oil fatty acids and glycerol with various lipases using 2 eq. of FFA and 1 eq. of glycerol after 24 hours at 40° C.

| | | Glycerides | | | | Residual Free fatty acids | | | |
| | | Area % | | Wt. % | | Area % | | Wt. % | |
| Lipase | % Conv. | EPA | DHA | EPA | DHA | EPA | DHA | EPA | DHA |
| --- | --- | --- | --- | --- | --- | --- | --- | --- | --- |
| PRL | 4.9 | 7.3 | 4.5 | 2.1 | 2.0 | 17.1 | 11.0 | 97.9 | 98.0 |
| PFL | 2.5 | 5.5 | 4.8 | 0.8 | 1.1 | 17.1 | 11.5 | 99.2 | 98.9 |

TABLE 9-continued

The progress of the direct esterification reaction under high vacuum of sardine oil fatty acids and glycerol with various lipases using 2 eq. of FFA and 1 eq. of glycerol after 24 hours at 40° C.

| | | Glycerides | | | | Residual Free fatty acids | | | |
| | | Area % | | Wt. % | | Area % | | Wt. % | |
| Lipase | % Conv. | EPA | DHA | EPA | DHA | EPA | DHA | EPA | DHA |
| --- | --- | --- | --- | --- | --- | --- | --- | --- | --- |
| LNL | 4.3 | 4.6 | 1.5 | 1.1 | 0.6 | 18.1 | 10.9 | 98.9 | 99.4 |
| ROL | 6.4 | 8.0 | 1.0 | 2.9 | 0.6 | 18.2 | 11.8 | 97.1 | 99.4 |
| CAL | 94.0 | 12.6 | 7.7 | 93.4 | 90.1 | 14.0 | 13.3 | 6.6 | 9.9 |
| ANL | 1.7 | 13.4 | 9.5 | 1.3 | 1.6 | 18.0 | 10.2 | 98.7 | 98.4 |

The results shown in Table 9 are in quite stark contrast to those shown in Table 8 for the same lipases.

Thus, the extent of the conversion was much lower for all the lipases, except CAL, and for none of the lipases was there any significant discrimination between EPA and DHA. It is considered that the lower activity of all the lipases except CAL is probably attributable to the very high vacuum employed removing the essential water content of the lipase with considerable detrimental effect on the activity of the lipase.

EXAMPLE 10

(Comparative)

In this experiment sardine oil ethyl esters were directly esterified with glycerol using a number of different lipases. The reactions were conducted under agitation at 40° C. for 24 hours under vacuum, using the lipase at a concentration of 10% and two equivalents of the ethyl esters per equivalent of glycerol. The results are presented in Table 10 below. The extent of conversion was based on the amount of residual ethyl esters present in the reaction mixture.

TABLE 10

Results of enzyme screening for the reaction of ethyl ester from sardine oil with glycerol after 24 hours at 40° C.

| Lipase under vacuum | % Conv. | Ethyl esters | | | Glycerides | | | Free fatty acids | | |
|---|---|---|---|---|---|---|---|---|---|---|
| | | % wt. | EPA (%) | DHA (%) | % wt. | EPA (%) | DHA (%) | % wt. | EPA (%) | DHA (%) |
| MML | 61.6 | 38.4 | 17.8 | 18.1 | 55.7 | 17.4 | 6.7 | 5.7 | 0.9 | 1.8 |
| CRL | 2.6 | 97.4 | 15.1 | 9.4 | 1.2 | 5.9 | 3.6 | 1.4 | 6.5 | 3.8 |
| RDL | 3.5 | 96.5 | 18.0 | 11.5 | 2.8 | 10.1 | 3.7 | 0.8 | 4.7 | 0.0 |
| ROL | 3.5 | 96.4 | 17.4 | 10.5 | 2.5 | 6.6 | 2.6 | 1.1 | 6.0 | 6.2 |
| PCL | 3.2 | 96.8 | 18.2 | 11.4 | 1.0 | 3.1 | 1.6 | 0.4 | — | — |
| PSL | 7.1 | 92.9 | 15.7 | 10.5 | 5.8 | 4.6 | 5.4 | 0.6 | — | — |
| PFL | 3.8 | 96.2 | 16.7 | 11.0 | 3.9 | 9.0 | 5.0 | 0.0 | — | — |
| MJL | 5.2 | 94.8 | 18.5 | 11.6 | 5.0 | 4.8 | 2.3 | 0.0 | — | — |
| PPL | 3.2 | 96.8 | 18.2 | 11.4 | 1.0 | 3.1 | 1.6 | 1.2 | 10.6 | 7.1 |

It is apparent from Table 10 that the glycerolysis reaction proceeded much slower in terms of conversion as compared to the direct esterification of free fatty acids with glycerol. Only MML displayed only appreciable conversion and the other lipases displayed very little or no activity.

This experiment shows that ethyl esters, although more advantageous and more readily available as raw material, do not represent a preferred starting material in this invention.

EXAMPLE 11

Example 1 was repeated using as the starting material a semi-raffinated tuna oil containing 5.2% EPA and 24.5% DHA. The results are given in Table 11 below.

TABLE 11

The progress of the direct esterification reaction of semi-raffinated tuna oil free fatty acids and glycerol with MML.

| | % Conv. | Glycerides | | | | Residual Free fatty acids | | | |
|---|---|---|---|---|---|---|---|---|---|
| | | Area % | | Wt. % | | Area % | | Wt. % | |
| Time | | EPA | DHA | EPA | DHA | EPA | DHA | EPA | DHA |
| 1 h | 16.8 | 3.4 | 1.6 | 12.0 | 1.3 | 5.1 | 24.5 | 88.1 | 98.7 |
| 2 h | 29.1 | 3.9 | 3.3 | 19.7 | 3.9 | 6.5 | 33.5 | 80.3 | 96.1 |
| 3 h | 40.5 | 3.9 | 2.0 | 29.3 | 4.0 | 6.4 | 32.4 | 70.7 | 96.0 |
| 4 h | 45.5 | 3.7 | 1.6 | 31.6 | 3.4 | 6.6 | 36.9 | 68.4 | 96.6 |
| 5 h | 51.1 | 3.7 | 1.9 | 35.8 | 4.5 | 7.0 | 41.3 | 64.2 | 95.5 |
| 6 h | 56.2 | 3.9 | 1.8 | 41.1 | 5.0 | 7.2 | 44.4 | 58.9 | 95.0 |
| 7 h | 57.6 | 3.6 | 1.7 | 39.5 | 4.8 | 7.4 | 45.7 | 60.5 | 95.2 |
| 11 h | 64.2 | 4.1 | 1.9 | 52.2 | 6.7 | 6.8 | 48.1 | 47.8 | 93.4 |
| 24 h | 74.2 | 5.2 | 2.8 | 71.4 | 10.3 | 6.0 | 71.1 | 28.6 | 89.8 |
| 48 h | 90.0 | 6.7 | 5.0 | 90.9 | 21.4 | 2.9 | 77.5 | 9.1 | 78.7 |

It will be seen that good conversion, with effective discrimination between EPA and DHA was obtained.

EXAMPLE 12

Example 1 was repeated once more using a crude fish oil containing 20.0% EPA and 7.2% DHA as starting material. The results are shown in Table 12.

TABLE 12

The progress of the direct esterification of crude fish oil free fatty acids and glycerol with MML.

| | % Conv. | Glycerides | | | | Residual Free fatty acids | | | |
|---|---|---|---|---|---|---|---|---|---|
| | | Area % | | Wt. % | | Area % | | Wt. % | |
| Time | | EPA | DHA | EPA | DHA | EPA | DHA | EPA | DHA |
| 1 h | 29.4 | 15.2 | 0.6 | 22.0 | 3.1 | 22.4 | 7.8 | 78.0 | 96.9 |
| 2 h | 56.4 | 19.7 | 1.1 | 50.2 | 10.3 | 25.2 | 12.8 | 49.8 | 89.7 |
| 3 h | 73.0 | 23.0 | 1.9 | 75.3 | 24.5 | 20.4 | 15.8 | 24.7 | 75.5 |
| 4 h | 78.4 | 23.5 | 2.4 | 83.0 | 32.5 | 17.4 | 18.4 | 17.0 | 67.5 |
| 5 h | 79.2 | 25.6 | 3.1 | 84.4 | 37.0 | 18.0 | 20.3 | 15.6 | 63.0 |
| 6 h | 82.1 | 25.6 | 3.1 | 87.5 | 37.5 | 16.7 | 23.9 | 12.5 | 62.5 |
| 7 h | 82.3 | 23.2 | 3.6 | 86.8 | 40.4 | 16.4 | 25.1 | 13.2 | 59.6 |
| 12 h | 82.3 | 22.7 | 5.4 | 86.9 | 48.5 | 15.8 | 26.7 | 13.1 | 51.5 |
| 24 h | 97.2 | 20.7 | 6.9 | 98.1 | 94.3 | 14.2 | 14.5 | 1.9 | 5.7 |
| 33 h | 97.2 | 19.5 | 6.4 | 97.7 | 94.9 | 15.7 | 11.8 | 2.3 | 5.1 |

It is clear from the results in Table 12 that glycerides of a highly favourable EPA to DHA ratio were obtained, with a high conversion rate. The illustrated process could therefore form the basis for a process for preparing a concentrate of EPA.

EXAMPLE 13

Example 1 was again repeated using free fatty acids from tuna oil (496 g) comprising 7.1% EPA and 29.4% DHA, glycerol (79.9 g) and MML (25 g). 68.3% conversion was obtained after 4.5 h. The glyceride mixture comprised 9.0% EPA and 11.2% DHA and the residual free fatty acids comprised 4.1% EPA and 54.9% DHA. The reaction mixture was introduced to a short-path distillation using a Leybold KDI,-4 still (Leybold A G, Hanau, Gemany) under a vacuum of 0.3 Pa. De-gassing was performed at 60° C. and a predistillation at 90° C. [The distillation at 90° C. gave a loss of only 6.2% DHA]. The residue from the pre-distillation was the distilled at 140° C. The results are demonstrated in Table 13.

TABLE 13

Results of short-path distillation of reaction mixture from direct esterification of free acid from tuna oil with glycerol using MML.

| | Fractions from distillation | | | Free fatty acids | | |
|---|---|---|---|---|---|---|
| Sample[1] | Wt. %[2] | % FFA[3] | % DHA[4] | WL % of total[5] | % DHA[6] | % EPA |
| D-140 | 42.0 | 85.0 | 43.5 | 73.3 | 52.6 | 6.1 |
| R-140 | 58.0 | 19.6 | 26.0 | 23.3 | 74.1 | 2.3 |

[1]Abbreviations: D-140 is the distillate at 140° C., R-140 is the residue from the distillation at 140° C.
[2]Weight percentage of fractions from each distillation individually.
[3]Weight percentage of free fatty acids in each fraction.
[4]DHA content of each fraction as based on area percentage from GC analysis.
[5]Weight percentage of free fatty acids as based on total weight of residual free fatty acids from the enzymatic reaction.
[6]DHA content of the free fatty acid counterpart of each fraction as based on area percentage from GC analysis.

As can be noticed from Table 13 the bulk of the fatty acids were distilled at 140° C. (73.3% as based on the total FFA content) and they comprised 52.3% DHA. This fraction was contaminated with 15% of monoglycerides of 3.3% DHA content. The residue still contains 23.3% FFA comprising 74.1% DHA. Still, as appears from table 13 a good enrichment of the DHA free fatty acid content is achievable through this process when applying the molecular distillation step.

An even better result is expected if the distillation is performed at a higher temperature of for instance 150–160° C. or at a better vacuum.

What is claimed is:

1. A process for preparing a free fatty acid fraction enriched in at least one of eicosapentaenoic acid (EPA) and docosahexaenoic acid (DHA) from a marine oil composition containing EPA and DHA in free acid form, comprising:
    a) forming a mixture of the marine oil composition, glycerol, and a catalytically effective amount of a lipase, the mixture being essentially free of organic solvent;
    b) agitating the mixture at a temperature effective to cause the glycerol to begin esterifying fatty acids in the mixture at different rates, while removing water of esterification from the mixture;
    c) halting the esterification reaction before all of the EPA and DHA is esterified and before the molar ratio of the fatty acids in the glycerol-esterified product in the reaction mixture is the same as the molar ratio of those fatty acids in the starting marine oil composition, thereby obtaining a product mixture, and
    d) subjecting the product mixture to molecular distillation to obtain a free fatty acid fraction and a glyceride fraction, the free fatty acid fraction being enriched in at least one of EPA and DHA, as compared to the marine oil composition, and the glyceride fraction being correspondingly enriched in the remaining fatty acids.

2. A process according to claim 1, wherein, in step a), the molar ratio of glycerol that is mixed with the free fatty acids in the marine oil composition is from 1:1.5 to 1:3.

3. A process according to claim 1, wherein, in step a), the molar ratio of glycerol that is mixed with the free fatty acids in the marine oil composition is from 1:1.5 to 1:2.5.

4. A process according to claim 1, wherein, in step a), the molar ratio of glycerol that is mixed with the free fatty acids in the marine oil composition is about 1:2.

5. A process according to claim 1, wherein the reaction of step b) is conducted at a pressure of below 6665 Pa.

6. A process according to claim 5, wherein the reaction of step b) is conducted at a pressure below 1333 Pa.

7. A process according to claim 6, wherein the reaction of step b) is conducted at a pressure of from 133.3 to 1333 Pa.

8. A process according to claim 7, wherein the reaction of step b) is conducted at a pressure of from 1.333 to 133.3 Pa.

9. A process according to claim 8, wherein the reaction of step b) is conducted at a pressure of from 1.333–13.33 Pa.

10. A process according to claim 1, wherein the reaction of step b) is conducted at a temperature of 20°–40° C.

11. A process according to claim 1, wherein said lipase is immobilized on a carrier.

12. A process according to claim 1, wherein said lipase is *Rhizomucor meihei*.

13. A process according to claim 1, wherein said lipase preferentially catalyses the esterification of EPA, as compared to DHA.

14. A process according to claim 1, wherein said lipase preferentially catalyses the esterification of DHA, as compared to EPA.

15. A process according to claim 1, wherein said lipase preferentially catalyses the esterification of both EPA and DHA, as compared to other fatty acids present in said marine oil composition.

16. A process according to claim 1, wherein said molecular distillation is performed at a temperature of 100°–200° C. under a vacuum of $1 \times 10^{-4} - 1 \times 10^{-2}$ mbar.

17. The process according to claim 1, wherein the fatty acid fraction obtained in step d) is subjected to an additional lipase catalyzed esterification step.

18. The process according to claim 1, wherein said lipase is selected from the group consisting of *Rhizomucor meihei* lipase, *Mucor javanicus* lipase, *Aspergillus niger* lipase, Pseudomonas sp lipase, *Pseudomonas flurescens* lipase, *Rhizopus oryzae* lipase and *Humicula lanuginosa* lipase.

19. The process according to claim 13, wherein said lipase is selected from the group consisting of *Rhizomucor meihei* lipase, *Mucor javanicus* lipase, and *Aspergillus niger* lipase.

20. The process according to claim 19, wherein said lipase is *Rhizomucor meihei* lipase.

21. The process according to claim 15, wherein said lipase is selected from the group consisting of Pseudomonas sp lipase, *Pseudomonas flurescens* lipase, *Rhizopus oryzae* lipase and *Humicula lanuginosa* lipase.

22. The process according to claim 16, wherein said molecular distillation is performed at a temperature of 140°–160° C.

23. The process according to claim 1, wherein the glyceride fraction obtained in step d) is subjected to saponification with aqueous alkali to convert at least a portion of the fraction into free fatty acids and lesser-esterified glycerol.

24. The process according to claim 1, wherein the glyceride fraction obtained in step d) is subjected to transesterification with a monohydric alcohol to form EPA and DHA esters of the monohydric alcohol.

25. The process according to claim 1, wherein said marine oil composition is a fish oil composition.

26. The process according to claim 1, wherein said marine oil composition contains a combined weight of EPA and DHA of 15 to 35 percent, based on the weight of the composition.

27. The process according to claim 26, wherein said marine oil composition contains a combined weight of EPA and DHA of 25 to 35 percent, based on the weight of the composition.

\* \* \* \* \*

UNITED STATES PATENT AND TRADEMARK OFFICE
CERTIFICATE OF CORRECTION

PATENT NO. : 6,518,049 B1
DATED : February 11, 2003
INVENTOR(S) : Gudmundur G. Haraldsson et al.

It is certified that error appears in the above-identified patent and that said Letters Patent is hereby corrected as shown below:

Title page,
Item [56], FOREIGN PATENT DOCUMENTS, "2303492 A" should read -- 2-303492 A --. "07203979 A2" should read -- 07-203979 A2 --.
OTHER PUBLICATIONS, "McNeill et al." "Polyunstaturated" should read -- Polyunsaturated --.

Column 3,
Line 46, "earned" should read -- carried --.
Lines 51 and 52, "1.333 Pa" should read -- 1333 Pa --.
Line 56, "front" should read -- from --.

Column 6,
Line 16, "5.6" should read -- 5.5 --.
Line 32, "Upozyme," should read -- Lipozyme, --.
Table 1, line 56, "61.9" should read -- 81.9 --.

Column 7,
Line 57, after "18.9," "5.6" should read -- 5.5 --.

Column 14,
Line 61, "Gemany)" should read -- Germany) --.

Column 15,
Line 45, "c) halting" should read -- c) discontinuing --.

Signed and Sealed this

Thirteenth Day of January, 2004

JON W. DUDAS
*Acting Director of the United States Patent and Trademark Office*